US00RE38623E1

(19) United States
(12) Reissued Patent
Hernandez et al.

(10) Patent Number: US RE38,623 E
(45) Date of Reissued Patent: Oct. 12, 2004

(54) STABILIZATION OF ASCORBIC ACID, ASCORBIC ACID DERIVATIVES AND/OR EXTRACTS CONTAINING ASCORBIC ACID FOR TOPICAL USE

(75) Inventors: Steven Hernandez, Blue Point, NY (US); Burt Shaffer, Huntington, NY (US)

(73) Assignee: Topix Pharmaceuticals, Inc., Amityville, NY (US)

(21) Appl. No.: 09/725,980

(22) Filed: Nov. 29, 2000

Related U.S. Patent Documents

Reissue of:

(64) Patent No.: 5,843,411
Issued: Dec. 1, 1998
Appl. No.: 08/796,784
Filed: Feb. 6, 1997

(60) Provisional application No. 60/011,441, filed on Feb. 9, 1996.

(51) Int. Cl.[7] ..... A61K 33/32

(52) U.S. Cl. ..... 424/59; 424/401; 424/456; 514/474; 514/844

(58) Field of Search ..... 424/59, 401, 456; 514/474, 844

(56) References Cited

U.S. PATENT DOCUMENTS 4,938,969 A * 7/1990 Schinisky et al. ..... 424/59
5,140,043 A * 8/1992 Darr et al. ..... 514/474
5,587,149 A * 12/1996 Punto et al. ..... 424/59

* cited by examiner

*Primary Examiner*—Shengjun Wang
(74) *Attorney, Agent, or Firm*—Alfred M. Walker

(57) ABSTRACT

A stable composition is provided to treat and/or prevent photo-aged skin and related skin disorders such as sunburn, wrinkles, poor skin tone and skin discoloration by topically applying to the skin the treatment composition containing an effective amount of a compound such as ascorbic acid, derivatives of ascorbic acid and/or extracts containing ascorbic acid, in a pharmaceutically acceptable vehicle containing a substantially anhydrous base having no water added. The anhydrous base stabilizes the compound, so that the compound remains effective for an effective period of time, even in the presence of exposure to water.

21 Claims, No Drawings

STABILIZATION OF ASCORBIC ACID, ASCORBIC ACID DERIVATIVES AND/OR EXTRACTS CONTAINING ASCORBIC ACID FOR TOPICAL USE

Matter enclosed in heavy brackets [ ] appears in the original patent but forms no part of this reissue specification; matter printed in italics indicates the additions made by reissue.

*This application is based upon provisional application Ser. No. 60/011,441, filed Feb. 9, 1996.*

FIELD OF THE INVENTION

The present invention is directed to a composition for stabilizing ascorbic acid, ascorbic acid derivatives and/or extracts containing ascorbic acid, in a stable delivery system for topical application to the skin. The composition prevents premature aging of the skin of humans, or may be used to treat photo-aged skin and resultant wrinkles and other sequelae.

BACKGROUND OF THE INVENTION

Treatment of photo-aged skin and resultant wrinkles and other sequelae with ascorbic acid and related derivatives has been discussed in the prior art. Among the most common treatment regimen is a topical application of ascorbic acid to affected areas of the skin in lotions, creams and other delivery vehicles, such as discussed in U.S. Pat. No. 5,140,043 of Darr et al for stable ascorbic acid compositions.

In Darr '043, it is noted that L-ascorbic acid prevents ultraviolet (UV) damage to the skin. In the discussion of the background art therein. Darr '043 states that ascorbic acid, also commonly known as Vitamin C, acts as an anti-oxidant to counteract the skin damaging effects of superoxide and hydroxyl radicals, which have been known to cause a wide variety of damaged skin conditions ranging from transitory sunburn to permanent wrinkles from photo-aged skin. According to Darr '043, these radicals destroy lipid membranes, break down DNA and inactivate beneficial enzymes which promote healthy skin conditions, citing Cerutti, D. et al. eds. *Oxy-radicals in Molecular Biology and Pathology,* (Alan Liss, publisher, New York, N.Y. 1988). Hayaishi, O. et al. eds., *Biological Role of Reactive Oxygen Species in Skin,* (Elsevier Press, New York, N.Y. 1987). Johnson Jr., J. E. et al. eds., *Free Radicals, Aging and Degenerative Diseases,* (Alan Liss publisher, New York, N.Y. 1986). Halliwell, B. et al. eds. *Free Radicals in Biology and Medicine,* (Clarendon Press, Oxford, U.K. 1985), and Sied, H., ed., *Oxidative Stress,* (Academic Press, 1985), among other cited publications therein.

Free radicals from ultraviolet light (UV) are known to increase with air pollution in areas of concentrated populations, thereby magnifying the problem. The free radicals are destructive in that the free radicals hydrolyse elastin fibers in the skin and desynthesize collagen in the lower dermal layers of the skin, thereby causing skin wrinkles and other damaging skin conditions.

In contrast, it has also been known that ascorbic acid is effective in counteracting the effects of free radicals upon the skin. Ascorbic acid absorbs ultraviolet (UV) radiation and at the same time stimulates collagen production.

However, ascorbic acid, such as Vitamin C, is difficult to stabilize for any significant period of time in pharmaceutical vehicles for topical delivery to the skin. Ascorbic acid loses potency and discolors easily in most delivery vehicles. Furthermore, ascorbic acid hydrolyzes when exposed to water.

The term "stable" is defined as a characteristic wherein a composition retains potency for the duration of a predetermined expiration period, as defined by generally accepted pharmaceutical protocols, such as "GMP", or "good manufacturing practices" as promulgated by various trade conventions, such as for example, the United States Pharmaceutical (USP) convention.

For example, for a topically applied skin care formulation, the expected duration of a predetermined expiration period should be at least eight months before the formulation loses significant potency.

In contrast Dar '043 only tested the product described therein for twelve weeks.

Moreover, as noted in Darr '043, ascorbic acid washes off easily when exposed to water, so that topical application at a sun-lit beach is generally futile, since swimming washes away the topically applied ascorbic acid.

Furthermore, in the past, ascorbic acid has been administered in high dosages to the skin, and has to be made every day because of its instability, thus increasing cost of its use.

Darr '043 discloses a method of stabilizing ascorbic acid in a water based delivery system with an ascorbic acid to water/carrier ratio of at least 1:1, preferably 2:1 to 10:1.

The ascorbic acid and water mix described in Darr '043 includes both water and a carrier, such as alkylene glycols, or alkylene glycols in combination with one or more derivatives of hydroxyalkyl-cellulose. However, the minimum amount of water in the product disclosed in Darr '043 is fifty (50) percent, since Darr '043 teaches at least a 1:1 ratio of water to carrier, preferably greater than fifty (50) percent, such as sixty seven (67) percent water in a 2:1 ratio, up to ninety two (91) percent water in a 10:1 water/carrier ratio.

In general, the carrier is described as being compatible with water, preferably distilled or deionized water without contaminants, which further de-stabilize ascorbic acid.

However, the disadvantage of the delivery vehicle in Darr '043 is that it is water-based, and therefore the ascorbic acid is still inherently unstable.

For example, while FIG. 1 of Darr '043 shows small drops in potency of L-ascorbic acid of less than 10 percent over seven weeks at room temperature of L-ascorbic concentrations of three (3), five (5) and ten (10) percent respectively. FIG. 1 shows a drop in potency of approximately 30 percent over seven weeks, from 100 percent to 70 percent, of L-ascorbic acid in a concentration of one (1) percent.

Moreover, FIG. 2 of Darr '043 shows all four samples of L-ascorbic acid having lost potency of at least ten (10) percent over eight (8) weeks at room temperature, when stored under controlled conditions in the dark.

Furthermore, while the testing in Darr '043 was conducted from between seven (7) and twelve (12) weeks duration, any viable over the counter consumer product requires in excess of twelve weeks from manufacture through distribution points to final retail sale, and must still afford the consumer a reasonable time to consume the contents of the product. Therefore, a loss in potency of the magnitude as shown in Darr '043 in such a short time span, raises serious questions as to the usefulness of the stability data obtained in predicted the potency of L-ascorbic acid at the time the consumer is able to use the product.

Therefore, the response of the ascorbic acid in the epidermals and dermis of the skin is not very effective, because of the presence of substantial amounts of water, which contribute to destabilization of the ascorbic acid.

OBJECTS OF THE INVENTION

It is therefore an object of the present invention to provide a stable composition and pharmaceutical delivery system for ascorbic acid, ascorbic acid derivatives and/or extracts containing ascorbic acid as effective treatments for photo-aged skin and related skin disorders.

It is yet another object to provide a topical preparation of ascorbic acid, ascorbic acid derivatives and/or extracts containing ascorbic acid for more effective treatment of photo-aged skin and related skin disorders.

It is yet a further object to provide a topical delivery vehicle for ascorbic acid, derivatives of ascorbic acid and/or extracts containing ascorbic acid, wherein the delivery vehicle is substantially anhydrous with no water added.

It is yet a further object to provide ascorbic acid, ascorbic acid derivatives and/or extracts containing ascorbic acid, in a composition wherein the ascorbic acid, ascorbic acid derivatives and/or extracts containing ascorbic acid remain effective for an extended period of time.

It is yet another object to improve over the disadvantages of the prior art.

BRIEF SUMMARY OF THE INVENTION

In keeping with these objects and others which may become apparent, according to the present invention, a new stable, long-lasting composition is provided as a pharmaceutical delivery vehicle for delivery of ascorbic acid, ascorbic acid derivatives and/or extracts containing ascorbic acid, to prevent and treat sun-damaged and photo-aged skin, and as a preventative and cosmetic for undamaged skin.

A method of preventing and/or treating photo-aged skin, sunburn, wrinkles and related skin disorders is provided by topical application of a lotion, cream, gel or pad applied formulation, preferably a substantially anhydrous composition, with no water added, containing effective amounts of ascorbic acid, ascorbic acid derivatives and/or extracts containing ascorbic acid, for topical application to the affected area of the skin. The composition of the present invention can also be used to prevent photo-aging of the skin.

Ascorbic acid, or its derivatives, such as ascorbic palmitate, sodium ascorbate, potassium ascorbate, ammonium ascorbate, triethanolamine ascorbate, ascorbyl phosphate or magnesium ascorbyl phosphate and related compounds, is applied in a pharmaceutically acceptable vehicle, in a concentration of from 0.1 percent by weight to 95 percent by weight, preferably 10–15 percent by weight, generally by frequent periodic application, such as by a once or twice daily application.

Instead of a substantially water based delivery system, the ascorbic acid, ascorbic acid derivatives and/or extracts containing ascorbic acid are provided in a substantially anhydrous base, with no added water. Because the components have a natural water sub-component, the base is not water free, but is substantially anhydrous, because the pre-existing water concentration does not generally exceed five (5) percent by weight of the total composition. To achieve the substantially anhydrous composition, no water is added, in contrast to the water-based composition in Darr '043.

The substantially anhydrous base protects the ascorbic acid, or its derivatives and/or extracts containing ascorbic acid, from degradation, instability, loss of potency and loss of color.

The topical pharmaceutical delivery vehicle includes a mixture of a base consisting essentially of a substantially anhydrous composition, with no water added, in combination with the ascorbic acid, ascorbic acid derivatives and/or extracts containing ascorbic acid, wherein the substantially anhydrous composition, with no water added, is provided in a range of from 0.1 percent by weight to 99.8 percent by weight, preferably about 30 percent by weight.

In the preferred embodiment, the substantially anhydrous base includes silicone compounds, which provide a unique, cosmetically elegant smooth, lustrous tactile feel when applied to the skin.

Preferably the substantially anhydrous composition, with no water added, includes silicones and derivatives of silicone chemistry. However, other substantially anhydrous composition, with no water added, may be utilized, such as other emollients, emulsifiers, surfactants, oils and waxes, polyols, binders, anti-oxidants or chelating agents.

Other inactive components may include preservatives, humectants, viscosity control aids, pH buffers and carrier solvents. However, certain pH buffers and solvents may also function as a substantially anhydrous base.

The resultant mixture is smooth feeling delivery vehicle which delivers the ascorbic acid or its derivatives to the skin in an effective and stable manner.

DETAILED DESCRIPTION OF THE PREFERRED EMBODIMENTS

In accordance with the present invention, a stable, long-lasting composition is provided as a pharmaceutical delivery vehicle for delivery of ascorbic acid to sun-damaged and photo-aged skin.

A method of treating photo-aged skin, sunburn, wrinkles and related skin disorders is also provided by topical application of a lotion, cream, gel or pad applied formulation, preferably a substantially anhydrous composition, with no water added, containing effective amounts of a compound selected from the group consisting of ascorbic acid, ascorbic acid derivatives and/or extracts containing ascorbic acid, for topical application to the affected area of the skin.

Ascorbic acid, or its derivatives, such as ascorbyl palmitate, sodium ascorbate, potassium ascorbate, ammonium ascorbate, triethanolamine ascorbate, ascorbyl phosphate or magnesium ascorbyl phosphate, ascorbic acid polypeptides, ascorbyl glucosamine, ascorbic acid polymers, esters of ascorbic acid, amides of ascorbic acid L-ascorbic acid, known as vitamin C, or other derivatives, or related compounds, including botanical or herbal extracts, such as extracts of acerola, citrus extracts, strawberry, which may supply L-ascorbic acid or its derivatives, is applied in a pharmaceutically acceptable vehicle, in a concentration of from 0.1 percent by weight to 95 percent by weight, preferably 10–15 percent by weight, generally by frequent periodic application, such as by a once or twice daily application.

Instead of a water based delivery system, the compound containing ascorbic acid, ascorbic acid derivatives and/or extracts containing ascorbic acid, is provided in a substantially anhydrous with no water added base without water. The base provides a unique cosmetically elegant topical vehicle which protects the ascorbic acid or its derivatives from degradation, instability, loss of potency and loss of color. The base includes a mixture of a substantially anhydrous composition, with no water added, with the compound, wherein the substantially anhydrous composition is provided in a range of from 0.1 percent by weight to 99.8 percent by weight, preferably about 30 percent.

Preferably, the substantially anhydrous composition, with no water added, includes silicones and derivatives of silicone chemistry, including but not limited to cyclomethicones (volatile silicones), linear silicones, dimethylpolysiloxane, dimethicone copolyols, silicone glycols, aminofunctional silicones, polymeric silicones, silicone waxes, such as high molecular weight dimethicones and silicone derivative waxes.

When various silicone compounds are used, a lustrous, elegant smooth tactile feel is achieved when the topical composition is applied to the skin.

Other substantially anhydrous compositions, with no water added, may be substituted for the silicones, such as other emollients, including but not limited to esters, amides, ethoxylated fats, mineral oil, petrolatum, vegetable fats and animal fats, such as hydrogenated tallow and lanolin.

Substantially anhydrous synthetic waxes, such as triglycerides and tribehin may be utilized. Polyols such as polyhydric alcohols and solvent such as mineral oil, glycerin and propylene glycol and sorbitol may be used.

Emulsifiers such as anhydrous polysorbate and PEG 60 hydrogenated castor oil may be employed, as well as anhydrous surfactants such as nonphenol.

Anti-oxidants, such as BHA, BHT, propylgallate, Vitamin E tocopherol, as well as chelating agents such as disodium EDTA, may also be used to further stabilize other substantially anhydrous bases. However, liquid or non-granular anti-oxidants, may be used as a substantially anhydrous base with ascorbic acid by themselves.

Fat soluble vitamins, such as substantially anhydrous Vitamins A, D and E and their esters or derivatives, may also be used as bases for the ascorbic acid based composition.

Moreover, pH buffers such as alkaline sodium citrate and magnesium citrate are effective as substantially anhydrous bases for the delivery vehicle.

Other inactive components may include preservatives, humectants, viscosity control aids, pH buffers and carrier solvents. However, as noted above, certain pH buffers and solvents may also act as an anhydrous base.

The resultant mixture is a comfortable delivery vehicle which delivers the ascorbic acid, its derivatives or extracts containing ascorbic acid to the skin in an effective and stable manner.

The following examples illustrate topically applied skin care products which can be prepared using conventional procedures from the following ingredients with typical ranges of acceptable percentages by weight and typical preferred percentage by weight shown. The formulations are illustrative only:

| Ingredient | Range(% w/w) | Preferred(% w/w) |
|---|---|---|
| Formulation #1: | | |
| Ascorbic acid | 0.1–95.0 | 10.0 |
| Cyclomethicone | 0.1–99.8 | 30.0 |
| Water (no water added) | 0–5.0 | 0.0 |
| Surfactant | 0–90.0 | 5.0 |
| Methylparaben (preservative) | 0.0–3.0 | 0.2 |
| Steareth-2 (emulsifier) | 0.0–10.0 | 3.5 |
| Gelene (viscosity aid) | 0.0–95.0 | 36.3 |
| Bentronite (binder) | 0.0–25.0 | 5.0 |
| Formulation #2: | | |
| Polyglyceryl methacrylate Gel | 0.0–99.0 | 60.0 |
| Ascorbic acid | 0.1–95.0 | 15.0 |
| Silicone Glycol | 0.1–60.0 | 15.0 |
| Water | 0.0 | 0.0 |

The present invention therefore includes a method for the prevention and/or treatment of photo-aged skin and related skin disorders, such as wrinkles, sunburn, poor skin tone and skin discoloration.

The method comprises steps of the topical application of suitable compositions containing ascorbic acid, its derivatives or extracts containing ascorbic acid, in a substantially anhydrous base, with no water added.

In general, the treatment composition suitable for use in accordance with the invention containing ascorbic acid, its derivatives or extracts containing ascorbic acid, may be applied in any dermatological acceptable vehicle such as a gel, lotion, cream or pad applied formulation, which may or may not be emulsified and may contain ingredients to improve, modify, or stabilize the formulation physically or cosmetically. Other suitable formulations will be apparent to those skilled in the art.

The treatment compositions of the invention will improve the condition of the skin to which it is applied, preferably by frequent periodical application over an extended period of time without undue irritation to the skin or any other side effects.

Generally, the topical applications are applied periodically such as one or two times per day.

Moreover, Table 1 shows the stability of examples of the composition. Stability tests were conducted of topical skin treatment compositions containing ascorbic acid, specifically L-ascorbic acid at 10%. The compositions were tested for percentage of stability as a function of shelf life in a closed jar at either room temperature or at an elevated temperature of from 40° C. to 45° C. Tests of the containers of the compositions at room temperature were conducted over a six month period and tests of the containers of the compositions at elevated temperature of from 40° C. to 45° C. were conducted over a three month period.

TABLE I

Composition No. 1:

a topical facial complex containing 10% of L-ascorbic acid.
a) Condition: maintained at room temperature in a ½ oz. clear jar with lined cap.
b) Test: ascorbic acid assay.
c) Recommended Percentage of Stability: 80.0%–110.0%
d) Resultant Percentage of Stability:

| 0 months | 3 months | 6 months |
|---|---|---|
| 95.6% | 90.1% | 90.4% |

Composition No. 1:

a topical facial complex containing 10% of L-ascorbic acid.
a) Condition: maintained at 40° C. to 45° C. in a ½ oz. clear jar with lined cap.
b) Test: ascorbic acid assay.
c) Recommended Percentage of Stability: 90.0%–110.0%
d) Resultant Percentage of Stability:

| 0 months | 1 month | 2 months | 3 months |
|---|---|---|---|
| 95.6% | 91.4% | 90.4% | 84.5% |

Composition No. 2:

a topical hand and body complex containing 10% of L-ascorbic acid.
a) Condition: maintained at room temperature in a 2 oz. container.
b) Test: ascorbic acid assay.
c) Recommended Percentage of Stability: 80.0%–110.0%
d) Resultant Percentage of Stability:

| 0 months | 3 months | 6 months |
|---|---|---|
| 98.5% | 92.4% | 90.2% |

TABLE I-continued

| Composition No. 2: | | | |
|---|---|---|---|
| a topical hand and body complex containing 10% of L-ascorbic acid. | | | |
| a) Condition: maintained at eleveated temperature from 40° C. to 45° C. in a 2 oz. container. | | | |
| b) Test: ascorbic acid assay. | | | |
| c) Recommended Percentage of Stability: 80.0%–110.0% | | | |
| d) Resultant Percentage of Stability: | | | |
| 0 months | 1 month | 2 month | 3 months |
| 98.5% | 95.0% | 91.1% | 84.0% |

Other changes to the present invention may be made without departing from the spirit or scope thereof, when read in conjunction with the appended claims.

We claim:

1. A topical composition consistently essentially of a mixture of a compound selected from the group consisting of ascorbic acid, derivatives of ascorbic acid and extracts containing ascorbic acid and a substantially anhydrous pharmaceutically acceptable base in an amount of above about 10% by weight of the composition.

2. The composition as in claim 1 wherein said substantially anhydrous base comprises a silicone.

3. The composition as in claim 2 wherein said substantially anhydrous base comprises a cyclomethicone.

4. The composition as in claim 2 wherein said substantially anhydrous base comprises a linear silicone.

5. The composition as in claim 2 wherein said substantially anhydrous base comprises dimethylpolysiloxane.

6. The composition as in claim 2 wherein said substantially anhydrous base comprises a dimethicone copolyol.

7. The composition as in claim 2 wherein said substantially anhydrous base comprises a silicone glycol.

8. The composition as in claim 2 wherein said substantially anhydrous base comprises an aminofunctional silicone.

9. The composition as in claim 2 wherein said substantially anhydrous base comprises an polymeric silicone.

10. The composition as in claim 1 wherein said substantially anhydrous base comprises an emollient.

11. The composition as in claim 1 wherein said substantially anhydrous base comprises an emulsifier.

12. The composition as in claim 1 wherein said substantially anhydrous base comprises a surfactant.

13. The composition as in claim 1 wherein said substantially anhydrous base comprise a liquid anti-oxidant.

14. The composition as in claim 1 wherein said substantially anhydrous base comprises as chelating agent.

15. The composition as in claim 1 wherein said substantially anhydrous base comprises a solvent.

16. The composition as in claim 1 wherein said substantially anhydrous base comprises a synthetic wax.

17. The composition as in claim 1 wherein said substantially anhydrous base comprises an alkaline anhydrous pH buffer.

18. The composition as in claim 1 wherein said substantially anhydrous base comprises a fat soluble vitamin.

19. The method of treating photo-aged skin and related skin disorders, wrinkles, sunburn, poor skin tone and/or skin discoloration, comprising the steps of applying topically to the area of the skin affected an effective amount of a treatment composition consistently essentially of a mixture of a compound selected from the group consisting of ascorbic acid, derivatives of ascorbic acid and extracts containing ascorbic acid and a pharmaceutically acceptable vehicle comprising a substantially anhydrous single phase carrier base, said compound being present in an amount of above about 10 percent by weight of the treatment composition.

20. The method according to claim 19, wherein said treatment composition is applied periodically to the skin area to be treated, said periodic treatment being applied in an amount as required to be efficacious.

21. The method according to claim 19, wherein said pharmaceutically acceptable vehicle including the substantially anhydrous base is provided in the group consisting of a cream, lotion, pad applied formulation of gel base.

* * * * *